United States Patent [19]
Fahlvik

[11] Patent Number: 5,855,868
[45] Date of Patent: Jan. 5, 1999

[54] METHOD OF $T_1$-WEIGHTED RESONANCE IMAGING OF RES ORGANS

[75] Inventor: Anne Kjersti Fahlvik, Oslo, Norway

[73] Assignee: Nycomed Imaging AS, Oslo, Norway

[21] Appl. No.: 625,223

[22] Filed: Apr. 1, 1996

[51] Int. Cl.$^6$ .................................................. A61B 5/055
[52] U.S. Cl. .................................. 424/9.322; 424/9.323; 424/646; 424/648
[58] Field of Search ............................. 424/9.322, 9.323, 424/646, 648; 436/173; 600/420; 428/551; 514/6

[56] References Cited

U.S. PATENT DOCUMENTS

| | | | |
|---|---|---|---|
| 4,452,773 | 6/1984 | Molday | 424/1.1 |
| 4,767,611 | 8/1988 | Gordon | 424/9 |
| 4,827,945 | 5/1989 | Groman et al. | 128/653 |
| 4,849,210 | 7/1989 | Widder | 424/9.32 |
| 4,863,715 | 9/1989 | Jacobsen et al. | 424/9 |
| 4,904,479 | 2/1990 | Illum | 424/490 |
| 4,925,678 | 5/1990 | Ranney | 424/493 |
| 5,069,216 | 12/1991 | Groman et al. | 424/9.322 |
| 5,160,725 | 11/1992 | Pilgrimm | 424/9 |
| 5,225,282 | 7/1993 | Chagnon et al. | 428/407 |
| 5,314,679 | 5/1994 | Lewis et al. | 424/9.322 |
| 5,328,681 | 7/1994 | Kito et al. | 424/9.322 |
| 5,349,957 | 9/1994 | Yudelson | 128/653.4 |
| 5,358,702 | 10/1994 | Unger | 424/9.322 |

FOREIGN PATENT DOCUMENTS

| | | |
|---|---|---|
| 0 525 199 | 2/1993 | European Pat. Off. . |
| 0 580 878 | 2/1994 | European Pat. Off. . |
| 94/21240 | 9/1994 | WIPO . |
| 96/04017 | 2/1996 | WIPO . |
| 96/09840 | 4/1996 | WIPO . |

OTHER PUBLICATIONS

Benderbous et al., *Radiologe,* Suppl. 2:35, S248–S252 (1995).
Weissleder et al., *Adv. Drug Rev.,* 16, 321–344 (1995).
Laniado et al., *Radiologe,* Suppl. s:35, S266–S270 (1995).
Hagspiel et al., *Radiology,* 196, 471–478 (1995).

*Primary Examiner*—Gary E. Hollinden
*Attorney, Agent, or Firm*—Bacon & Thomas, PLLC

[57] ABSTRACT

The invention provides a method of contrast enhanced MR angiography of the human or non-human animal body, said method comprising administering into the vasculature thereof a contrast effective amount of a contrast agent composition comprising magnetic particles having a $r_2/r_1$ ratio of no more than 5, and, at a time when sufficient of said magnetic particles remain in the vasculature to provide positive contrast enhancement thereof in a $T_1$-weighted image while sufficient magnetic particles have been taken up into an organ of the reticuloendothelial system to provide negative contrast enhancement thereof in said $T_1$-weighted image, generating a $T_1$-weighted image magnetic resonance image of at least said organ.

19 Claims, 1 Drawing Sheet

A. LIVER VESSELS
PRE CONTRAST

B. LIVER VESSELS
35 MIN POST CONTRAST
4 mg Fe / kg

A. LIVER VESSELS
PRE CONTRAST

B. LIVER VESSELS
20 MIN POST CONTRAST
5 mg Fe / kg

METHOD OF $T_1$-WEIGHTED RESONANCE IMAGING OF RES ORGANS

FIELD OF THE INVENTION

This invention relates to a method of generating enhanced images in magnetic resonance (MR) imaging procedures, in particular MR angiography, and to the use of magnetic particles as contrast agents in contrast media for such procedures.

BACKGROUND OF THE INVENTION

In diagnostic imaging modalities, such as X-ray, MR and ultrasound, the use of contrast agents to enhance image contrast, e.g. between different organs or tissues or between healthy and unhealthy tissue, is a well established technique.

In MR imaging, the contrast agents used generally have a contrast generating effect due to their effects on the characteristic relaxation times $T_1$ (spin-lattice) or $T_2$ (spin-spin) of the imaging nuclei which are responsible for the MR signals which are detected and manipulated to yield images.

In $T_1$ and $T_2$ dependant images, the function for signal intensity is dependent on $T_1$ in such a way that, absent other effects, a decrease in $T_1$ would lead to an increase in signal intensity. However the signal intensity function is dependent on $T_2$ in such a way that, again absent other effects, a decrease in $T_2$ (or $T_2^*$) would lead to a decrease in signal intensity.

For the purposes of this specification references to $T_2$ and $T_2$ dependency shall where appropriate cover $T_2^*$ and $T_2^*$ dependency as well.

Thus, while MR contrast agents may reduce both $T_1$ and $T_2$, for a given imaging sequence one effect may dominate, and where the $T_1$ decrease dominates the agent may be referred to as a $T_1$ or positive contrast agent while where the $T_2$ decrease dominates the agent may be called a $T_2$ or negative contrast agent.

The first parenteral MR contrast agents available commercially were low molecular weight lanthanide chelates, such as GdDTPA and GdDTPA-BMA, which distribute extracellularly and generally have an MR signal intensity increasing effect in the zones into which they distribute. Such contrast agents are thus commonly used in $T_1$-weighted imaging sequences in which their image brightening effect is optimal.

Later, the use of magnetic particles (e.g. superparamagnetic iron oxide particles) as $T_2$ or negative agents for investigation of the liver was proposed in view of the ability of the organs of the reticuloendothelial system (RES) to abstract particulate materials from the blood. Thus, for example, the use of magnetic particles in $T_2$-weighted imaging of the liver and spleen was proposed in U.S. Pat. No. 4,849,210 (Widder). Widder taught that the particle should be administered and allowed to accumulate at the liver before a $T_2$-weighted imaging sequence is used to generate images in which the particles, localized image darkening effect serves to enhance contrast, for example between healthy liver parenchyma and liver tumour tissue.

Recently there has been much interest in the development of MR contrast agents which assist visualization of the vasculature, i.e. so-called blood pool or angiographic contrast agents, by enhancing contrast between blood vessels and surrounding tissue or organs. The utility of an MR angiographic contrast agent depends largely upon its relaxivity profile and pharmacokinetic behaviour. Ideally the agent should remain in the intravascular space for a period of time sufficient to allow image generation, i.e. the blood half life should be sufficient to provide an adequate imaging window. For this purpose the low molecular weight chelates are inadequate because of their rapid distribution to the whole extracellular volume.

Macromolecular paramagnetic agents (e.g. lanthanide chelates of polychelants) have been found to be operable as MR angiographic contrast agents but only have the contrast enhancing effect of brightening blood vessels.

It has now been found however that certain magnetic particles having low $r_2/r_1$ ratios (i.e. ratios of $T_2$ relativity to $T_1$ relativity) may be used particularly effectively in liver angiography, the study of the vasculature within the liver in RES angiography (or the study of other phagocytosing organs which have appropriate vasculature), by virtue of their opposed contrast generating effects in the two environments of blood vessel (before RES uptake) and liver tissue (after RES uptake). Using a $T_1$-weighted imaging sequence, a positive signal enhancement of the vessels containing the magnetic particles is achieved whereas in the organs of the reticuloendothelial system, once the particles accumulate, there is a negative contrast effect. Thus the vessel to liver contrast is increased significantly.

To achieve this double contrast effect, it is important that the magnetic particles used as the contrast agent should comprise particles which, unlike those of Widder (supra) or of other commercially available magnetic particle MR contrast media, have a low $r_2/r_1$ ratio and a prolonged blood residence half-life and that the images generated should comprise (i.e. be or include) $T_1$-weighted images.

SUMMARY OF THE INVENTION

Thus viewed from one aspect the invention provides a method of contrast enhanced MR angiography of the human or non-human (preferably mammalian, avian or reptilian) animal body, said method comprising administering into the vasculature thereof a contrast effective amount of a contrast agent composition comprising magnetic particles having a $r_2/r_1$ ratio of no more than 5, and, at a time (preferably within 50 minutes of administration of the $r_2/r_1 \leq 5$ particles, and especially preferably within 40 minutes of administration) when sufficient of said magnetic particles remain in the vasculature to provide positive contrast enhancement thereof in a $T_1$-weighted image while sufficient magnetic particles have been taken up into an organ of the reticuloendothelial system to provide negative contrast enhancement thereof in said $T_1$-weighted image, generating a $T_1$-weighted image magnetic resonance image of at least said organ.

Viewed from a further aspect there is provided the use of magnetic particles having a $r_2/r_1$ ratio of no more than 5 for the manufacture of a magnetic resonance imaging contrast medium for use in a method of diagnosis which includes administering said medium into the vasculature of a human or non-human animal body, and, at a time when sufficient of said magnetic particles remain in the vasculature to provide positive contrast enhancement thereof in a $T_1$-weighted image while sufficient magnetic particles have been taken up into an organ of the reticuloendothelial system to provide negative contrast enhancement thereof in said $T_1$-weighted image, generating a $T_1$-weighted image magnetic resonance image of at least said organ.

DETAILED DESCRIPTION

The $r_2/r_1$ threshold required by the method of the invention is important as conventional high $r_2/r_1$ ratio magnetic particles do not appear to function adequately as positive contrast agents in $T_1$-weighted angiographic imaging.

The rate of magnetic particle uptake by the RES is highly dependent on the size and surface characteristics of the particles and may also be dosage dependant. Thus particles with a high first pass liver clearance, administered at a dosage below the RES saturation limit, may largely be cleared from the vasculature in a single passage through the liver. Such particles administered at higher dosages may show prolonged blood residence times (due for example to RES saturation) with successive drops in blood concentration as the clearance function returns. Particles coupled to opsonization inhibitors or blood lifetime prolonging agents may instead show a more constant blood clearance rate. For the purposes of the present invention what is required is that, once sufficient magnetic particles are taken up by the RES to provide negative contrast, magnetic particles satisfying the $r_2/r_1$ ratio criterion should remain in the vasculature long enough to allow an adequate imaging window. The required length of the imaging window will of course depend upon the image generation technique (e.g. the selected pulse sequence) and the MR imaging apparatus used.

By "magnetic particle" is meant a particle, either a composite of magnetic and non-magnetic materials or being of magnetic material alone. By "magnetic material" is meant a material which exhibits ferromagnetic, ferrimagnetic or, more preferably, superparamagnetic behaviour. A magnetic particle may thus contain a single magnetic crystal, either free or coupled to or coated with a non-magnetic (i.e. non ferro, ferri or superparamagnetic) material, or a plurality of magnetic crystals, either freely aggregated or coupled to, coated with, embedded in or otherwise associated with a non-magnetic material.

For the purposes of the invention, the magnetic particles are preferably composite particles majoritatively or predominantly (e.g. substantially exclusively) comprising a single magnetic crystal coupled to a non-magnetic material.

For parenteral use, the size and size distribution of the magnetic crystals and particles and the chemical nature of the surface of the overall particle are of great importance in determining the contrast generation efficacy, the blood half-life, and the biodistribution and biodegradation of the contrast agent. Ideally the magnetic crystal size is within the single domain size range (such that the particles are superparamagnetic and thus have no hysteresis and a reduced tendency to aggregate) and the overall particle size distribution is narrow so that the particles have uniform biodistribution and bioelimination and uniform contrast effects in like environments. Preferably, the magnetic particles should be coupled to or provided with a surface coating of a material which modifies particle biodistribution, e.g. by prolonging blood half-life, or by increasing stability, or which acts as a targeting vector causing active or passive distribution to a target site, such as for example the RES.

Particularly preferably the particles should be coupled to or provided with a coating of a blood half-life prolonging material.

In a further embodiment of the invention, besides the magnetic particles which meet both the $r_2/r_1$ ratio and sufficient blood residence time criteria set out above (the first particles) one may also administer into the vasculature of the subject under study further magnetic particles (the second particles) having different $r_2/r_1$ ratios and/or blood half-lifes from the first particles. In particular, as the second particles one may utilize particles having a shorter blood half-life than the first particles and optionally having a larger $r_2/r_1$ ratio.

Thus for example one may use two sets of particles having similar magnetic properties but with one set (the first particles) coupled to or coated with a blood half-life prolonging material and the other set (the second particles) not. In this embodiment, the first and second particles may be administered together or separately, but preferably together. The second set of particles is then more rapidly extracted from the blood by the RES and as a result a greater proportion of the imaging window of the first particles for blood pool visualization can be used for liver vessel imaging angiography.

This combination of sets of magnetic particles having different blood half-lifes is new and forms further aspects of the invention. Viewed from a first of these aspects the invention provides a diagnostic composition comprising magnetic particles and a physiologically tolerable carrier or excipient, characterised in that said composition contains a first plurality of magnetic particles having an $r_2/r_1$ ratio of no more than 5 and a blood half-life of up to 24 hours, e.g. up to 250 minutes, and a second plurality of magnetic particles having a blood half-life lower, preferably at least 50% lower, than that of said first plurality. Particularly preferably the second particles should be particles having a high first pass effect and especially preferably the first particles should incorporate an opsonization inhibitor or other blood lifetime prolonging material.

Viewed from the second of these further aspects the invention also provides a diagnostic composition pack comprising a first composition comprising a first plurality of magnetic particles having an $r_2/r_1$ ratio of no more than 5 and a blood half-life of up to 24 hours, e.g. up to 250 minutes, together with a physiologically tolerable carrier or excipient, and separately a second composition comprising a second plurality of magnetic particle together with a physiologically tolerable carrier, said second plurality of magnetic particles having a blood half-life lower than that of said first plurality for simultaneous, separate or sequential use in a method of MR imaging.

Where such second particles are used, they may but need not comply with the $r_2/r_1$ ratio requirement placed on the first particles. One may accordingly use as the second particles the relatively large (and thus lower blood half-life) conventional iron oxide agents (SPIOs) which comprise multiple magnetic crystals and have higher $r_2/r_1$ ratios and have been used as $T_2$ agents. Such SPIOs have been widely described in the literature (see for example Hagspiel et al. Radiology 196: 471–478 (1995) and Laniado et al. Radiologe, Suppl. 2:35, S266–S270 (1995)) and are available for example as Endorem from Guerbet SA. Alternatively for the second particles one can use the newer ultra small iron oxide agents (USPIOs) which comprise particle containing single superparamagnetic crystals. USPIOs have also been widely described in the literature (see Weissleder et al. Adv. Drug Rev. 16: 321–334 (1995) and Benderbous et al. Radiologe, Suppl 2:35, S248–S252 (1995)) and are under trial for example as AMI227 (Sinerem) by Guerbet SA.

Subject to the $r_2/r_1$ limitations for the first particles referred to above, the magnetic crystals in the magnetic particles used according to the invention may be particles of any material capable of showing ferri, ferro or superparamagnetic behaviour.

The magnetic crystals will preferably be of any precipitable magnetic metal oxide or oxide hydroxide, including mixed metal compounds, for example compounds as discussed in U.S. Pat. No. 4,827,945 (Groman), EP-A-525199 (Meito Sangyo), EP-A-580878 (BASF) and PCT/GB94/02097 (Nycomed) or by U.S. Pat. No. 5,160,725 (Pilgrimm)

or WO94/21240 (Pilgrimm). Particular mention in this regard may be made of magnetic iron oxide compounds of formula $$(M^{II}O)_n(M^{III}{}_2O_3)$$

where $M^{II}$ and $M^{III}$ are transition or lanthanide metals in the II or III valence state, at least one of which is Fe, and n is zero or a positive number, or more particularly of formula $$(M^{II}O)_nFe_2O_3(M^{III}{}_2O_3)_m$$

where $M^{II}$ is a divalent metal such as Fe, Mg, Be, Mn, Zn, Co, Ba, Sr, and Cu, $M^{III}$ is a trivalent metal such as Al, Yb, Y, Mn, Cr or a lanthanide, and n and m are each zero or a positive number.

Preferably the magnetic crystals are iron oxides of formula $(FeO)_nFe_2O_3$ where n is in the range 0 to 1, typified by maghemite ($\gamma$-$Fe_2O_3$) and magnetite ($Fe_3O_4$) or are mixtures of such magnetic iron oxides.

Mean crystal sizes, i.e. of the magnetic core material, should generally be in the range 1 to 50 nm, preferably 1 to 20 nm and especially preferably 2 to 15 nm and, for use as blood pool agents, the mean overall particle size including any coating material should preferably be below 250 nm, especially preferably below 100 nm, more especially below 30 nm. Typically, the magnetic crystals may be produced by liquid phase precipitation, generally in a solution of a polymeric coating agent (e.g. using a co-precipitation technique such as that described by Molday in U.S. Pat. No. 4,452,773).

Alternatively, and preferably, the co-precipitation technique described in GB 9600427 (copy filed herewith) will be used, especially for the preparation of particles containing a blood lifetime prolonging material. This technique involves precipitation in a branched polymer containing aqueous medium and subsequently cleaving the polymer to release composite particles comprising magnetic crystals and a cleaved polymer coating. The composite particles may simultaneously or subsequently be coupled to a blood lifetime prolonging material, such as polyethylene glycol (PEG).

The non-magnetic material in composite magnetic particles used according to the invention may be any physiologically tolerable material or combination of materials with which the composite particles have the required biodistribution and pharmacokinetic profile. Generally such non-magnetic materials will comprise natural, semi-synthetic or synthetic polymers, e.g. carbohydrates, carbohydrate derivatives, proteins, polyalkylene oxides and derivatives thereof polyaminoacids, and block copolymers.

Where, as is generally desired, the magnetic particles are composites of magnetic crystals and a biotolerable polymer, the base is preferably added to an aqueous medium which contains the metal ions and the polymer. Alternatively, the base and polymer may be combined and the metal ions subsequently added.

Using the preferred method of GB 9600427, the composite particles produced comprise single supermagnetic crystals coated with a cleaved polymer, e.g. starch, coating.

These polymer-coated particles can be used as the first particles in the method of the invention. However, as the first particles it is preferable to use particles coupled to a blood life time prolonging polymer, either as a single "coating" material as suggested by Pilgrimm (supra) and by Illum in U.S. Pat. No. 4,904,479, or as a second "coating" material as suggested in GB 9600427.

Examples of materials which may be used in this way include carbohydrates such as oligo- and polysaccharides, as well as polyamino acids, oligo- and polynucleotides and polyalkylene oxides (including poloxamers and poloxamines) and other materials proposed by Pilgrimm in U.S. Pat. No. 5,160,725 and WO-94/21240, by Nycomed in PCT/GB94/02097, by Bracco in U.S. Pat. No. 5,464,696 and by Illum in U.S. Pat. No. 4,904,479.

Particularly preferably, the second coating material is a natural or synthetic structural-type polysaccharide, a synthetic polyaminoacid or a physiologically tolerable synthetic polymer as described in PCT/GB94/02097 or a stabilizer substance as described by Pilgrimm or Illum (supra). Particularly preferably the second coating material is a polyalkyleneoxide (e.g. a poloxamer, poloxamine, a polyethyleneglycol, etc.) or a heparinoid, and especially preferably such a material carrying a functional group, e.g. an oxyacid (e.g. sulphur, carbon or phosphorus oxyacid) function, which permits the coating material to bind chemically or adsorb to the composite particles and especially to the core magnetic crystals. In this regard particular mention may be made of methoxy-PEG-phosphate (MPP) and other polyalkyleneoxide materials described by Pilgrimm in U.S. Pat. No. 5,160,725 and WO-94/21240.

The molecular weight of the second coating material has been found not to be particularly critical and may conveniently be in the range 0.1 to 1000 kD, but materials having molecular weights of 0.3 to 20 kD, especially 0.5 to 10 kD and most especially 1 to 5 kD, are preferred, for example polyalkylene oxide materials having at least 60 alkylene oxide repeat units.

The weight ratio of the second coating material to the magnetic crystals is preferably in the range 0.02 to 25 g/g, especially 0.4 to 10 g/g and particularly 0.5 to 8 g/g.

The first particles used according to the invention should have an $r_2/r_1$ ratio of no more than 5 (measured at 0.5T and 37° C.), preferably no more than 4, especially preferably no more than 3 and most preferably no more than 2.5.

The relaxivity of magnetic crystal containing particles varies with the size and composition of the magnetic crystals, the number of crystals per magnetic particle and the size and composition of any non-magnetic component of the particle (e.g. any polymer coating) as well as with temperature and applied magnetic field. Typically for known superparamagnetic materials $r_2/r_1$ may be in the range 1 to 100 at 0.5T and 37° C.

Typically, $T_1$-weighted image generation will be effected about 1 minute to 24 hours, preferably 2 minutes to 4 hours, especially preferably 3 to 60 minutes and particularly preferably up to 50 minutes after administration of the magnetic particles.

The time delay between magnetic particle administration and $T_1$-weighted image generation is to allow sufficient magnetic particles to be taken up by the RES organs of interest to provide negative contrast therein. Alternatively put, $T_1$-weighted image generation will preferably be at a time when the positive contrast enhancement corresponds to a signal (or image) intensity increase of at least 80%, more preferably at least 100%, especially preferably at least 150%, while the negative contrast enhancement corresponds to a signal (or image) intensity decrease of at least 20%, more preferably at least 30%, especially preferably at least 35%.

Generally speaking, for intravascular administration, a delay of ⅙ $T_{1/2}$ to $T_{1/2}$, preferably ⅓ to ⅔ $T_{1/2}$, where $T_{1/2}$ is the blood half-life of the particles, will be adequate.

The first particles used according to the invention should preferably have a blood half-life up to 24 hours, e.g. up to 250 minutes. As the model for this measurement the rabbit may be used. However it is of course preferred that the particles' blood half-life in the species under investigation should similarly lie within this range. For fast imaging techniques or where the RES organ of interest has been preloaded with magnetic particles, the first particles need not have a particularly extensive blood half-life. In this regard half-lifes of as low as 1 minute may be adequate. Generally first particles having half-lifes of at least 5 or more especially at least 10 minutes may be convenient to use. Very long half life particles, e.g. particles having half lifes of at least 30 minutes, e.g. at least 50 minutes or even as long as 24 hours, may be used. Particularly conveniently however where first particles alone are used and are administered in a single injection, first particles having blood half-lifes of 5 to 180 or more particularly 10 to 120 minutes may be used.

Alternatively first particles having a high first pass effect may conveniently be used at dosages above the RES saturation limit.

Where first and second particles are administered separately, no delay from administration of the first particles to image generation may be necessary. The second particles in this case may be administered considerably in advance, e.g. up to 24 hours beforehand. If they have very short blood half-lifes the second particles may be administered simultaneously or even after the first particles. In general, where second particles not meeting the $r_2/r_1$ ratio criterion of the first particles are used, they will be administered at least twice their half-life, preferably at least five times their half-life before the $T_1$-dependent image is generated in order that they are by then substantially cleared from the blood. Where the second particles do meet the $r_2/r_1$ criterion, such substantial clearage is desirable but not necessary.

For the second particles, if they do not satisfy the $r_2/r_1$ criterion then if administered simultaneously or subsequent to the first particles they should have a shorter half-life than the first particles and preferably should have a high first pass effect. If administered in advance, the shorter half-life may not be necessary. In any event the dosage size and timing should be such that high $r_2/r_1$ particles are substantially cleared from the vasculature before the $T_1$-weighted image is generated.

In other words, the blood lifetime criterion for the first particles is that they must have a sufficient, but not too long, blood circulation time in order to give an acceptable imaging window, the period during which sufficient magnetic particles (first or second) have been taken up by the RES organ to provide negative contrast in the RES organ tissue whilst sufficient first particles are still circulating in the blood to provide positive contrast in the blood in a $T_1$-weighted, i.e. $T_1$ and $T_2$ dependent, image.

The magnetic particles will generally be administered in compositions in a conventional pharmaceutical form, e.g. suspension, emulsion, powder etc. which may contain aqueous vehicles (such as water for injections) and/or ingredients to adjust osmolality, pH, viscosity, and stability. Ideally, the composition is in suspension form with the suspension being isotonic and isohydric with blood. For example, an isotonic suspension can be prepared by the addition of salts like sodium chloride, low-molecular weight sugars like glucose (dextrose), lactose, maltose, or mannitol or a soluble fraction of the coating agent or a mixture of these. Isohydricity can be achieved by the addition of acids like hydrochloric acid or bases like sodium hydroxide if only a minor adjustment of pH is required. Buffers such as citrate, acetate, borate, tartrate, and gluconate may also be used. The chemical stability of the particle suspension can be modified by the addition of antioxidants like ascorbic acid or sodium pyrosulphite. Excipients may also be added to improve the physical stability of the preparation. Most frequently used excipients for parenteral suspensions are surfactants like polysorbates, lecithin or sorbitan esters, viscosity modifiers like glycerol, propyleneglycol and polyethylene glycols (macrogols), or cloud point modifiers, preferably non-ionic surfactants.

The compositions will advantageously contain the magnetic crystals at a diagnostically effective metal concentration, generally 0.1 to 250 mg Fe/ml, preferably 0.5 to 100 mg Fe/ml, and especially preferably 1 to 75 mg Fe/ml.

For the method of the invention, the dosage used will be a contrast effective dosage. Generally this will lie in the region 0.05 to 30 mg Fe/kg bodyweight, preferably 0.1 to 15 mg Fe/kg and especially preferably 0.25 to 8 mg Fe/kg.

Where first and second particles are used, these may conveniently be used in a weight ratio (of magnetic crystals) of from 1 to 10 to 10 to 1, preferably 10 to 1 to 1 to 1.

The particles may be injected or infused into the vasculature by conventional means. However if imaging of RES organs such as lymph nodes is required, some localised injection of particles to promote RES uptake by the organs of interest may be desirable. Thus besides simply the liver and spleen, other RES organs such as lymph nodes and bone marrow may be imaged by the method of the invention.

To obtain the double contrast achieved according to the invention, $T_1$ and $T_2$ dependant images should be generated. As is conventional in the field of MR imaging $T_1$ and $T_2$ dependant images may be weighted to emphasise the dependence of the signal intensity on $T_1$ or $T_2$. The resulting images are generally referred to as $T_1$-weighted and $T_2$-weighted images. For the purposes of the present invention an image will be adequately $T_1$-weighted when the first particles in circulation provide positive contrast in the image.

While the method of the present invention is particularly concerned with generation of $T_1$-weighted images (i.e. images in which RES organs will have negative contrast and the blood vessels in and adjacent these organs will have positive contrast), it will of course be beneficial also to generate $T_2$-weighted images as further diagnostically useful information may be extracted from such images in which both the RES organs and the blood vessels will have negative contrast. Similarly, pre-contrast (or no contrast) images will desirably be generated. Desirably also temporally spaced post contrast images will be generated in order to allow the time dependence of particle uptake by the RES to be followed.

The various publications referred to herein are hereby incorporated by reference.

EXAMPLES

Figure 1:
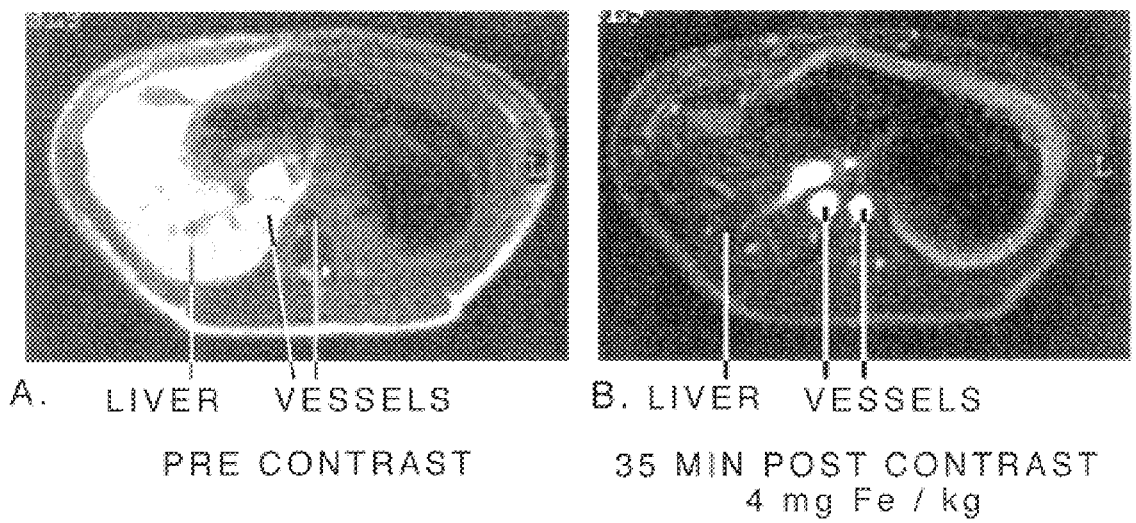
FIG. 1A and B are pre- and post contrast $T_1$-weighted images of the pig abdomen.

The invention will now be described further with reference to the following non-limiting Examples:

Example 1

Gel preparation steps: starch solution preparation and heating to 55° C., addition of iron chloride to starch solution, addition of ammonium hydroxide to iron/starch solution, heating of reaction mixture to 87°–90° C. and product cooling/gel neutralization.

A. Preparation of Starch Solution
1. Suspend 50 grams of soluble potato starch (CAS No. 9005-84-9) in 850 grams of boiling deionized water and mix.
2. Bring to the boil and immediately on boiling place the starch solution in a 55° C. water bath.

B. Addition of Iron and Ammonium Hydroxide to Starch
1. Dissolve 9.0 grams of $FeCl_3.6H_2O$ and 3.3 grams of $FeCl_2.4H_2O$ (2:1 molar ratio FeIII to FeII) in a total volume of 50 mL of deionized water.
2. After starch solution has cooled to a steady 55° C., pour the iron solution into the starch solution, mix thoroughly and add 50 ml of 30% (conc.) $NH_4OH$.
3. Heat the resulting solution so as to increase the temperature to 89° C. over 2 hours and maintain at 89° C. for a further 50 minutes.
4. After the 170 minute heating on the water bath, a) chill overnight at 4° C. to set gel, or b) cool to ambient temperature and neutralize with acid (see below).

C. Gel Washing Procedure (where gel is not acid neutralized)
Wash set gel by pumping cold deionized water through settled gel suspension until pH is less than 8.5.

D. Alternative Neutralization Process
Cool mixture to below 40° C., neutralize with acid.

E. Gel Oxidative Cleavage with Sodium Hypochlorite
A dose titration of the amount of sodium hypochlorite (hypo) per gram of gel can be done on a new lot to optimize production. Magnetic particle production is assessed by photon correlation spectroscopy (PCS) for size and dispersity, and by determination of water proton relaxation rates.
   a. For example, 1.8 mls of 5% hypo per 12.5 mgs Fe/5 gms of gel. Adjust volume of hypo for concentration of available chlorine and mgs Fe in 5 grams of gel.
   b. Weigh out gel, add hypochlorite and heat in water bath at 70° C. for 45 minutes.
   c. Add 8M urea (0.8 ml/5 gms of gel) after heating. Urea inactivates excess hypochlorite.
   d. Diafilter using a membrane (MW cutoff<100 kD) until all free Fe and CHO is removed.

F. Analysis
Samples are then subjected to analysis. Material prepared in this way has the characteristics outlined in Table 1:

TABLE 1

| Analysis | Result |
| --- | --- |
| Composition | |
| Iron (Fe) | 6.4 mg/ml |
| Mossbauer spectroscopy | predominantly nano crystals of gamma-$Fe_2O_3$ |
| Carbohydrate (CHO) | 3.6 mg/ml |
| CHO:Fe (weight ratio) | 0.57 |
| PURITY (Supernatant from particles centrifuged on CsCl density gradient of 1.4 g/ml) | |
| % Free Fe | 0% |
| % Free CHO | 0% |
| SIZE (Iron Oxide Core) | |
| Predicted from $r_2/r_1$ | 8 nm |
| NMRD* | 7 nm |
| LFI** | 6.24 ± 0.74 nm |
| Calculated from Magnetization | 5.7–5.8 nm |
| SIZE (Whole Particle) | |
| Photon Correlation Spectroscopy | 11.5 nm |
| Sedimentation velocity | 42.6 Svedberg Units |
| Sedimentation velocity | 42.6 Svedberg Units |
| RELAXIVITY (at 40° C. and 0.47 T) | |
| $r_1$ | 16.34 $(mM \cdot sec)^{-1}$ |
| $r_2$ | 28.04 $(mM \cdot sec)^{-1}$ |
| $r_2/r_1$ | 1.72 |
| STABILITY++ at 4° C. | >6 months |
| Saturation Magnetization | 60 emu/gm FeOx |

*Nuclear Magnetic Relaxation Dispersion
**Lattice Fringe Imaging
++Less than 5% sediments down on centrifugation at 12000 × g for 5 minutes.

With NMRD, the longitudinal relaxation rate ($1/T_1$) is measured as a function of magnetic field strength in the range 2.35 Gauss to 1.2 Tesla. See for example Koenig et al. NMR Spectroscopy of Cells and Organisms, Vol. II, page 75, R.K. Gupta (Ed), CRC Press, 1987 and Koenig et al. Progress in NMR Spectroscopy 22: 487–567 (1990).

Example 2
Prolonged blood lifetime contrast agent
Methoxy PEG phosphate (MPP) (mol. wt. 5 kD) was added to an aqueous suspension of particles produced according to Example 1 at the desired ratio of MPP to iron oxide (FeOx) (2 gms MPP/gm FeOx), incubated for 15 hrs at 37° C. with constant rotation and then stored at 4° C. until used.

If desired the particles can be autoclave sterilised at 121° C. for 15 minutes.

Example 3
Results of blood half life tests on particles of Examples 1 and 2
Mice were injected via tail vein with 100 μL samples at 1 mg Fe/mL of the preparations of Examples 1 and 2. At timed intervals, animals were euthanized, blood samples were collected and pooled from two mice and $1/T_1$ was measured. From $1/T_1$ values the half lives ($T_{1/2}$) were determined. The results are set out in Table 2 which includes for comparison the results for conventional MSM particles:

TABLE 2

| gm MPP/gm FeOx | $T_{1/2}$ (min) |
| --- | --- |
| 0 | 27.9 |
| 2 | 48.9 + 3.8 |
| MSM | 3.8 |

: Mean ± an estimated standard error in the linearity of the $T_{1/2}$ curve fitting.
MSM: Conventional co-precipitated magnetic starch particles.

Example 4
Contrast agent composition
MPP coated particles produced according to Example 2, diluted to an iron concentration of 10 mg FeOx/mL with 5% dextrose solution and sterile filtered before injection.

Example 5
Image generation
A contrast agent composition produced according to Example 4 was administered intravenously into the pig at a dosage of 4 mg Fe/kg bodyweight. Pre and 35 minutes post contrast $T_1$-weighted MR images were recorded at 1.5T, Turbo-FLASH, TR/TE/TI/flip 15 ms/4.1 ms/846 ms/25° and appear as FIGS. 1A and 1B hereto. The liver appears bright in the left of the pre-contrast image. In the post contrast image, the liver parenchyma is dark while the blood vessels running through it appear very bright.

Example 6

Image generation

Figure 2:
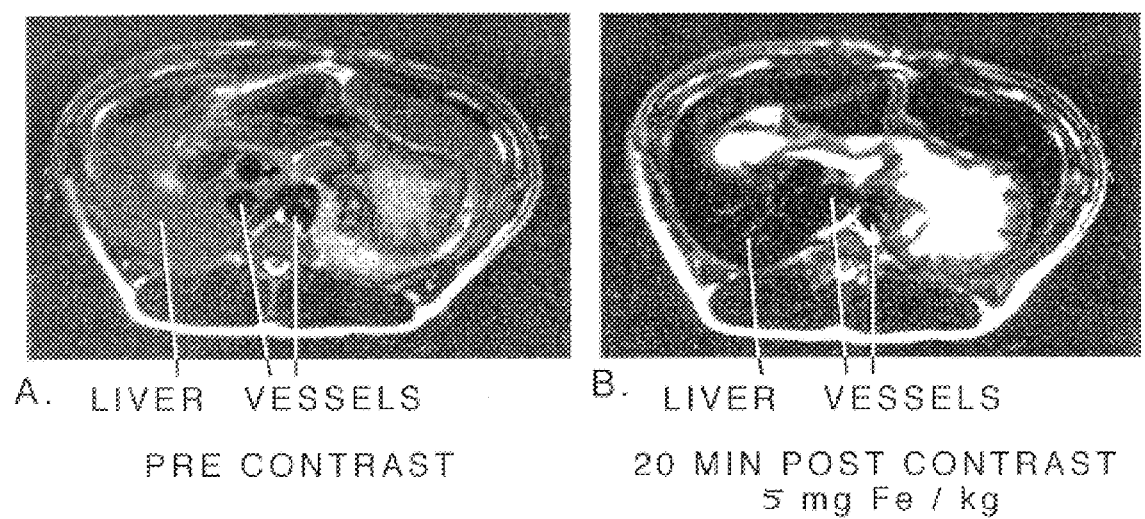
FIGS. 2A and B are pre- and post contrast $T_2$-weighted images of the pig abdomen.

A contrast agent composition produced according to Example 4 was administered intravenously into the pig at a dosage of 5 mg Fe/kg bodyweight. Pre and 20 minutes post contrast $T_2$-weighted MR images were recorded at 1.5T fast spin echo, TR/TE 1800 ms/100 ms and appear as FIGS. 2A and 2B hereto. Pre contrast, the liver parenchyma appears lighter than the blood vessels; post contrast both liver parenchyma and blood vessels appear dark. Comparison between FIGS. 1B and 2B allows differentiation between blood vessels in the liver and other non-parenchymal items.

Example 7

Combined contrast agent composition

MPP coated particles produced according to Example 2 are combined with particles produced according to Example 1 in a weight ratio (of FeOx) of 5:1, diluted to an iron concentration of 10 mg FeOx/mL with 5% dextrose solution and sterile filtered.

In place of the particles of Example 1 one may use conventional MSM or commercially available magnetic particles such as those available from Guerbet SA under the trade name Endorem.

I claim:

1. A method of contrast enhanced MR angiography of the human or non-human animal body, said method comprising administering into the vasculature thereof a contrast effective amount of a contrast agent composition comprising magnetic particles having a $r_2/r_1$ ratio of no more than 5, and, at a time when sufficient of said magnetic particles remain in the vasculature to provide positive contrast enhancement thereof in a $T_1$-weighted image while sufficient magnetic particles have been taken up into an organ of the reticuloendothelial system to provide negative contrast enhancement thereof in said $T_1$-weighted image, generating a $T_1$-weighted magnetic resonance image of at least said organ.

2. A method as claimed in claim 1 wherein said organ is the liver.

3. A method as claimed in claim 1 wherein said organ is a lymph node.

4. A method as claimed in claim 1 wherein a $T_2$-weighted image of at least said organ is also generated.

5. A method as claimed in claim 1 wherein said composition comprises magnetic particles having a $r_2/r_1$ ratio of no more than 5 and which are provided with an opsonization inhibitor or blood lifetime prolonging material.

6. A method as claimed in claim 5 wherein said composition comprises magnetic particles having a $r_2/r_1$ ratio of no more than 5 and which are provided with a polyoxyalkylene blood lifetime prolonging material.

7. A method as claimed in claim 1 wherein said magnetic particles exhibit superparamagnetic properties.

8. A method as claimed in claim 7 wherein said magnetic particles are composite particles comprising magnetic crystals and a biotolerable polymer.

9. A method as claimed in claim 8 wherein said biotolerable polymer is an oligo or polysaccharide.

10. A method as claimed in claim 9 wherein said polymer is an oxidatively cleaved starch.

11. A method as claimed in claim 8 wherein said composite particles further comprise an opsonization inhibitor or blood lifetime prolonging material.

12. A method as claimed in claim 11 wherein said composite particles comprise a polyalkyleneoxide blood lifetime prolonging material.

13. A method as claimed in claim 1 wherein said $T_1$-weighted image is generated at a time from 1 minute to 24 hours after administration of said magnetic particles having an $r_2/r_1$ ratio of no more than 5.

14. A method as claimed in claim 1 wherein said $T_1$-weighted image is generated at a time up to 50 minutes after administration of said magnetic particles having an $r_2/r_1$ ratio of no more than 5.

15. A method as claimed in claim 1 wherein said $T_1$-weighted image is generated at a time when said positive contrast enhancement corresponds to an image intensity increase of at least 80% and said negative contrast enhancement corresponds to an image intensity decrease of at least 20%.

16. A method as claimed in claim 1 wherein said $T_1$-weighted image is generated at a time when said positive contrast enhancement corresponds to an image intensity increase of at least 100% and said negative contrast enhancement corresponds to an image intensity decrease of at least 30%.

17. A method as claimed in claim 1 wherein said $T_1$-weighted image is generated at a time when said positive contrast enhancement corresponds to an image intensity increase of at least 150% and said negative contrast enhancement corresponds to an image intensity decrease of at least 30%.

18. A method as claimed in claim 1 wherein the $r_2/r_1$ ratio of said magnetic particles having a $r_2/r_1$ ratio of no more than 5 is no more than 3.

19. A method as claimed in claim 1 wherein the $r_2/r_1$ ratio of said magnetic particles having a $r_2/r_1$ ratio of no more than 5 is no more than 2.5.

* * * * *